(12) United States Patent
Prescott

(10) Patent No.: US 8,403,916 B2
(45) Date of Patent: Mar. 26, 2013

(54) SURGICAL INSTRUMENT HAVING A MAGNETICALLY DRIVEN DETACHABLE TOOL ASSEMBLY

(75) Inventor: Anthony D. Prescott, Arlington, TN (US)

(73) Assignee: Enteroptyx, Memphis, TN (US)

( * ) Notice: Subject to any disclaimer, the term of this patent is extended or adjusted under 35 U.S.C. 154(b) by 527 days.

(21) Appl. No.: 12/693,531

(22) Filed: Jan. 26, 2010

(65) Prior Publication Data

US 2010/0217245 A1 Aug. 26, 2010

Related U.S. Application Data

(60) Provisional application No. 61/155,665, filed on Feb. 26, 2009.

(51) Int. Cl.
*A61C 1/12* (2006.01)
(52) U.S. Cl. ............... 606/1; 433/133; 335/306
(58) Field of Classification Search ............... None
See application file for complete search history.

(56) References Cited

U.S. PATENT DOCUMENTS

| | | | |
|---|---|---|---|
| 4,232,535 A | 11/1980 | Caldwell | |
| 4,486,176 A * | 12/1984 | Tardieu et al. | 433/133 |
| 4,568,642 A * | 2/1986 | DeForrest et al. | 433/132 |
| 4,705,038 A | 11/1987 | Sjostrom et al. | |
| 4,811,736 A | 3/1989 | Griggs et al. | |
| 4,964,839 A | 10/1990 | Gloor | |
| 4,995,877 A | 2/1991 | Ams et al. | |
| 5,263,218 A | 11/1993 | Guiliani et al. | |
| 5,405,348 A | 4/1995 | Anspach, Jr. et al. | |
| 5,569,967 A * | 10/1996 | Rode | 310/103 |
| 5,609,602 A * | 3/1997 | Machemer et al. | 606/171 |
| 5,796,188 A | 8/1998 | Bays | |
| 6,047,456 A | 4/2000 | Yao et al. | |
| 6,126,670 A | 10/2000 | Walker et al. | |
| 6,425,761 B1 | 7/2002 | Eibofner | |
| 6,517,560 B1 * | 2/2003 | Toth et al. | 606/171 |
| 6,722,668 B2 | 4/2004 | Huggins et al. | |
| 6,887,244 B1 | 5/2005 | Walker et al. | |
| 7,294,947 B2 | 11/2007 | Corbin, III et al. | |
| 2010/0094306 A1* | 4/2010 | Chang et al. | 606/90 |
| 2011/0125176 A1* | 5/2011 | Yates et al. | 606/170 |

* cited by examiner

*Primary Examiner* — Henry M Johnson, III
*Assistant Examiner* — Scott T Luan
(74) *Attorney, Agent, or Firm* — Gordon & Jacobson, PC

(57) ABSTRACT

A medical instrument for use on a patient. The medical instrument includes a housing having a proximal end and a distal end, an electric motor mounted to the housing having a drive shaft rotatable about a drive axis, a drive magnet fixed to the drive shaft of said motor which rotates with the drive shaft about the drive axis, and a tool assembly coupled to the housing via a tool mount. The tool mount orients the tool assembly relative to the housing whereby guided rotational, translational, and/or oscillary motion of a tool within the tool assembly is achieved via the structure of the tool mount in conjunction with a magnetic coupling between magnets attached to both the motor and the tool.

40 Claims, 9 Drawing Sheets

SURGICAL INSTRUMENT HAVING A MAGNETICALLY DRIVEN DETACHABLE TOOL ASSEMBLY

CROSS-REFERENCE TO RELATED APPLICATIONS

This application claims the benefit of U.S. Provisional App. No. 61/155,665, filed Feb. 26, 2009, which is hereby incorporated by reference herein in its entirety.

BACKGROUND OF THE INVENTION

1. Field of the Invention

This invention relates broadly to powered medical instruments. More particularly, this invention relates to a medical instrument having a drive mechanism and tool assemblies which detachably mount to and magnetically couple with the drive mechanism.

2. State of the Art

Powered medical instruments known in the art utilize a wide variety of mechanisms to transfer power to move a medical tool operably disposed at the distal end of the instrument. The efficacy of a given mechanism is not only whether the desired movement of the medical tool is achieved, but also whether such mechanism adversely effects the longevity and/or efficiency of the medical instrument. Powered medical instruments generally employ some type of motor, power supply, medical tool, mechanisms for transferring power from the motor to the medical tool, and mechanisms for protecting and/or directing movement of the medical tool.

SUMMARY OF THE INVENTION

The present invention provides a medical instrument for use during a variety of surgical procedures, including those, e.g., on the skull, in the middle ear, in the sinus, and during arthroscopic procedures. The medical instrument includes a housing, a motor mounted to the housing, a drive magnet coupled to and rotated by the motor, a tool mount detachably coupled to the housing, and a replaceable tool assembly detachably coupled to the mount. The replaceable tool assembly includes a tool magnet and a medical tool disposed at opposite ends of an elongate shaft. The tool assembly is positioned by the tool mount with the tool magnet in magnetic communication with the drive magnet, whereby rotation of the drive magnet by the motor causes movement of the tool magnet, shaft, and tool.

More particularly, the housing of the surgical instrument is preferably an elongate, hollow, hermetically sealed metal or plastic structure which preferably defines sealed power connectors at a proximal end and a male portion at a distal end.

The motor includes a drive shaft rotatable about a drive axis. The drive magnet is fixed to the drive shaft of the motor whereby rotation of the drive shaft by the motor rotates the drive magnet about the drive axis. The motor is preferably situated inside the sealed housing with the drive shaft and the drive magnet situated inside the male taper portion at the distal end of the housing. The motor is coupled to a power supply via a power cable coupled to the sealed power connectors.

The tool mount defines a female portion at a proximal end which mates with the male portion of the housing, preferably in a frictional taper lock. The tool mount also defines a female bore at a distal end for receiving and positioning the tool assembly at a desired angle relative to the drive axis of the motor.

The tool assembly preferably includes a tool holder, a plastically deformable outer metal tube extending from a proximal end within the tool holder through the tool holder to a distal end, and a continuous bearing sleeve fixed within the outer metal tube to the inside surface of the metal tube. The bearing sleeve extends from a proximal end inside the tool holder, through the metal tube, to a distal end beyond the distal end of the metal tube. The elongate shaft of the tool assembly extends from a proximal end inside the tool holder, through the bearing sleeve, to a distal end beyond the distal ends of the metal tube and the bearing sleeve. The shaft is rotatable within the bearing sleeve about a shaft axis.

The tool magnet of the tool assembly is preferably situated within the tool holder and fixed to the proximal end of the elongate shaft proximal of the metal tube and the bearing sleeve. The tool magnet rotates with the shaft within the tool holder, preferably about a tool magnet axis aligned with the shaft axis. The tool magnet is also preferably cylindrically shaped, has a diameter, and is magnetized with opposite polarity on opposite sides of the diameter.

The medical tool is fixed to the distal end of the shaft, and thus rotates and/or longitudinally translates, and/or rotationally oscillates with the shaft. The medical tool may be a cutter, a drill, a file, or any of a number of other similar devices as further discussed below.

During operation, rotation of the drive shaft and drive magnet about the drive axis by the motor induces movement of the tool magnet. The structure of the tool mount and tool assembly in conjunction with the forces applied to the tool magnet via the magnetic coupling between the drive magnet and the tool magnet guide the movement of the tool in rotation, oscillation, and/or longitudinal translation on or about the shaft axis as further discussed below. The rotation or translation of the shaft within the flexible bearing sleeve minimizes frictional resistance, and thus increases the longevity and efficiency of the tool assembly as well as the power requirements needed to move the tool at a specific speed and/or in a given motion/direction.

The invention includes a speed reducer which can be optionally mounted between the housing and the mount. The speed reducer reduces the angular velocity transferred from the drive magnet to the tool magnet. The speed reducer includes an input magnet in magnetic communication with the drive magnet, a planetary gear drive mechanically coupled to the input magnet, and an output magnet mechanically coupled to the gear drive. The proximal end of the speed reducer couples to the distal end of the housing, and the distal end of the speed reducer couples to the proximal end of the tool mount, which then detachably couples to tool assembly as discussed above. The mount and tool assembly position the tool magnet in magnetic communication with the output magnet of the speed reducer. In operation, the motor rotates the drive shaft and drive magnet about the drive axis. The rotating drive magnet induces rotation in the input magnet of the speed reduction assembly. Rotation of the input magnet actuates the planetary gear drive, which, through a series of mechanical gears, produces a decreased angular velocity of the output magnet of the gear drive. The rotating output magnet induces movement of the tool magnet, which causes movement of the tool as discussed above. In this manner, a high speed motor may be utilized in conjunction with a tool that benefits from reduced speed operation by selecting the appropriate speed reducer.

The invention may also be presented as a kit with one or more mounts and one or more tool assemblies. For example, one tool assembly may be provided for achieving an oscillating rotational motion of the tool in the sinus passages of a patient for removing material therefrom. In this tool assembly, at least one attachment pin is provided to the side of the tool magnet. The tool holder defines at least one slot for slidably receiving the at least one attachment pin. When the slot extends in a generally perpendicular direction relative to the shaft axis, rotation of the drive magnet by the motor causes limited rotation (oscillation) of the tool and longitudinal translational motion of the tool is prevented.

Another tool assembly may be provided for achieving longitudinal translational motion of a tool to, for example, file down a bone surface. In this tool assembly, the tool holder defines at least one slot extending in a generally parallel direction relative to the shaft axis, which prevents rotation of the tool about the shaft axis but allows for limited longitudinal translation of the tool along the shaft axis.

Additional objects and advantages of the invention will become apparent to those skilled in the art upon reference to the detailed description taken in conjunction with the provided figures.

DETAILED DESCRIPTION

Figure 1:
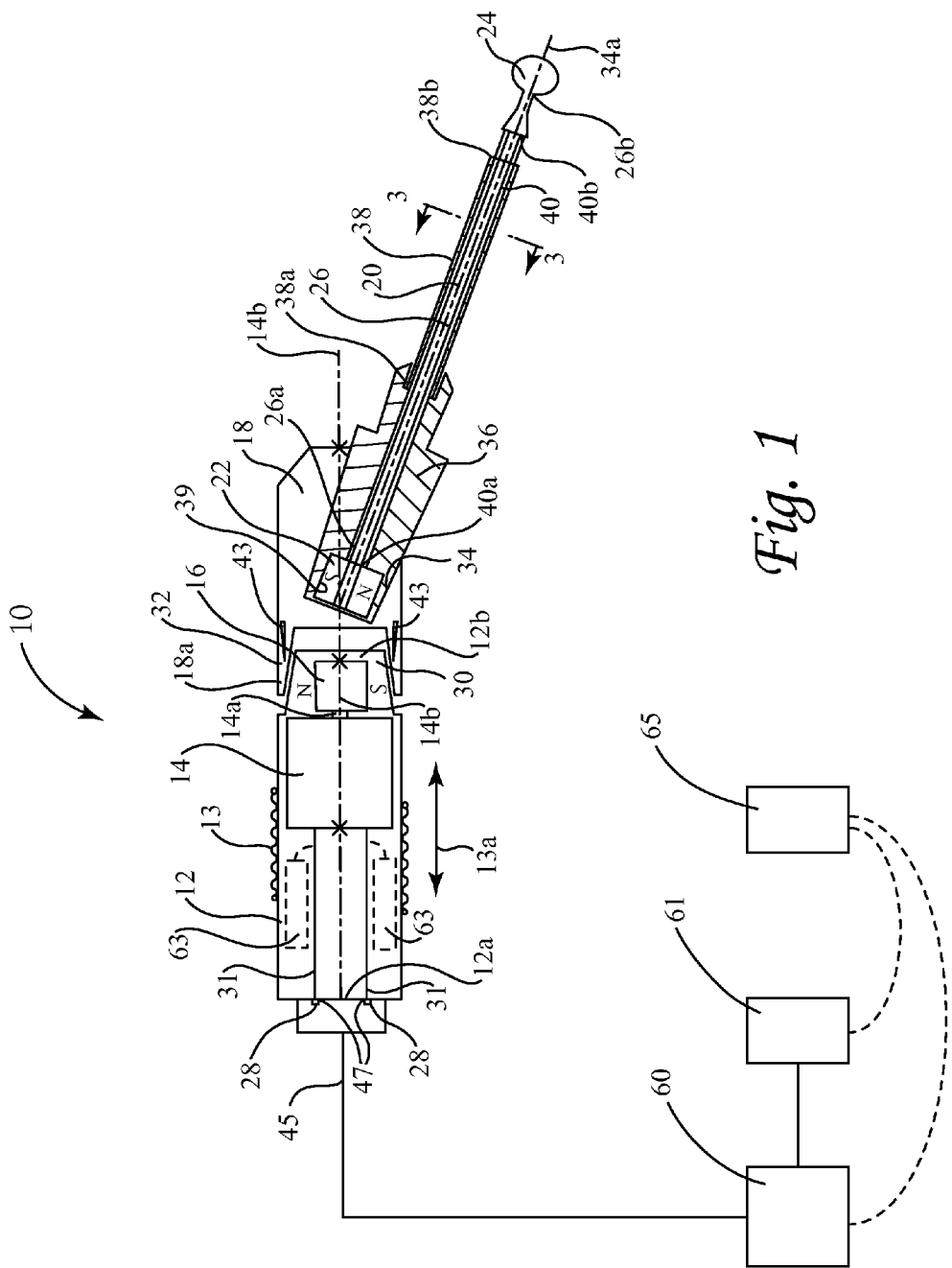
FIG. 1 is a schematic view of the preferred embodiment of the invention.

Turning now to FIG. 1, a medical instrument 10 according to the invention is shown. The instrument 10 includes a housing 12, an electric motor 14 mounted to the housing 12, a drive magnet 16 coupled to and rotated by the motor 14, a tool mount 18 detachably coupled to the housing 12, and a replaceable tool assembly 20 coupled to the mount 18. The replaceable tool assembly 20 includes a tool magnet 22 and a medical tool 24 disposed at opposite ends of an elongate shaft 26. The tool assembly 20 is positioned by the mount 18 with the tool magnet 22 in magnetic communication with the drive magnet 16, whereby rotation of the drive magnet 16 by the motor 14 causes movement of the tool magnet 22, shaft 26, and tool 24.

More particularly, the housing 12 of the surgical instrument 10 preferably comprises an elongate, hollow, hermetically sealed metal or plastic structure which defines one or more hermetically sealed power connectors 28 at a proximal end 12a and a male taper portion 30 at a distal end 12b. The housing 12 is hermetically sealed to protect the motor 14 and driver magnet 16, particularly during sterilization. The housing 12 optionally includes a resilient sleeve 13 for gripping the instrument 10 and reducing any vibrations which may be caused by operation of the instrument 10. The sleeve is preferably made of silicone and may be longitudinally advanced about the outer surface of the housing 12 in the direction shown by the arrows 13a so that a user can adjust the distance between the tool 24 and the user's hand.

The electric motor 14 includes a drive shaft 14a rotatable about a drive axis 14b. The drive shaft 14a and the drive magnet 16 fixed at its distal end are situated inside the male taper portion 30 at the distal end 12b of the housing 12. Wires 31 extending from the motor 14 connect to the power connectors 28 at the proximal end 12a of the housing 12. The power connectors 28 are attached to a power supply 60 via a power cable 45. Sealant 47 is applied at the edges of the power connectors 28 to hermetically seal the housing 12.

The drive magnet 16 is preferably cylindrically shaped and magnetized with opposite polarity (north and south) on opposite sides of its diameter as designated by the letters N and S in FIG. 1. The drive magnet 16 encircles the drive shaft 14a of the motor 14, and has a central axis which is co-axial with the drive axis 14b.

Figure 2:
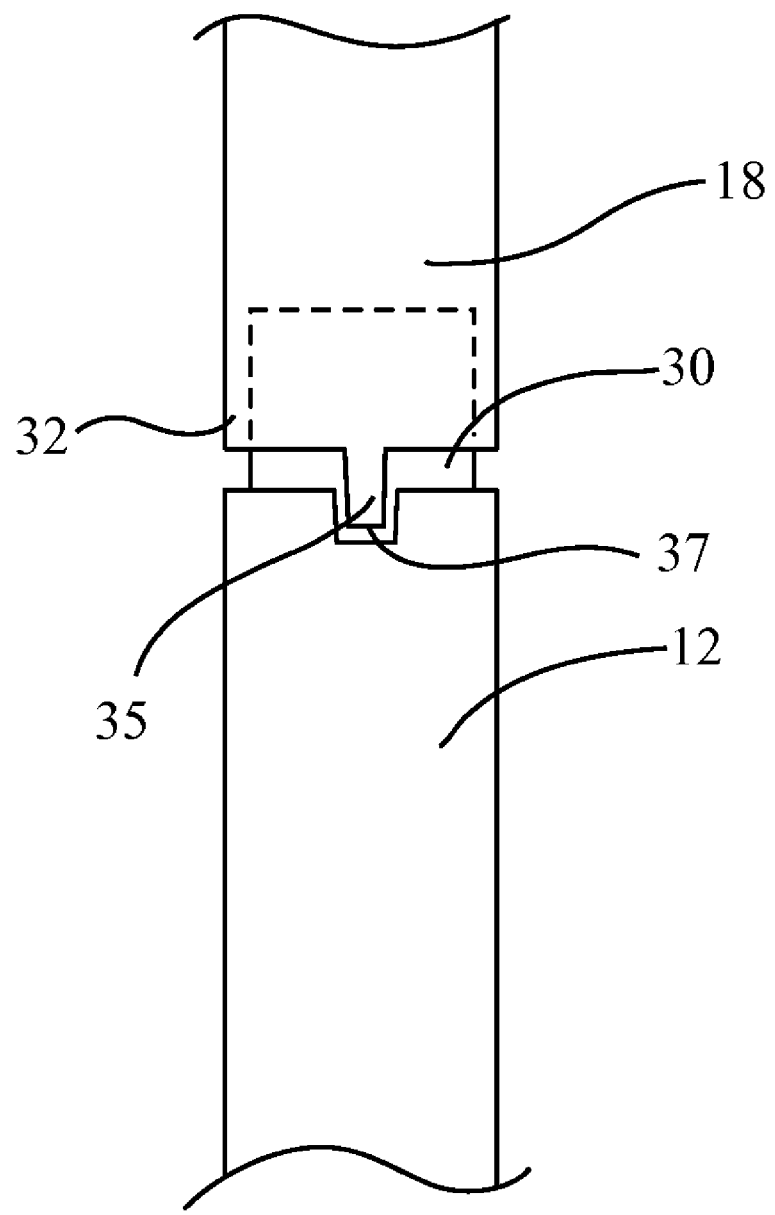
FIG. 2 is a top truncated view of the mount and housing of the invention.

The tool mount 18 is preferably made from PEEK plastic and defines a female portion 32 at a proximal end 18a which mates with the male taper portion 30 of the housing 12 in a frictional taper lock. The taper lock may be similar to, for example, a leur lock. The tool mount 18 may also define one or more expansion slots 43 which allow the female portion 32 to expand slightly to accommodate the male taper portion 30 of the housing 12. The mount 18 is meant to be fairly rigidly coupled to the housing 12, and must be strong enough to withstand forces transmitted through the tool assembly 20 while maintaining the tool magnet 22 in a fixed orientation relative to the housing 12. While the frictional locking of the male taper portion 30 and the female portion 32 is sufficient, rotation or other movement of the mount 18 may be further prevented with a tab in notch arrangement as shown in FIG. 2. FIG. 2 shows an enlarged top view of the mount 18 coupled to the housing 12 with the male taper portion 30 of the housing 12 partly recessed inside the female portion 32 of the mount 18 and a tab 35 extending from the female portion 32 of the mount 18 received in a slot 37 defined by the housing 12.

Figure 3:
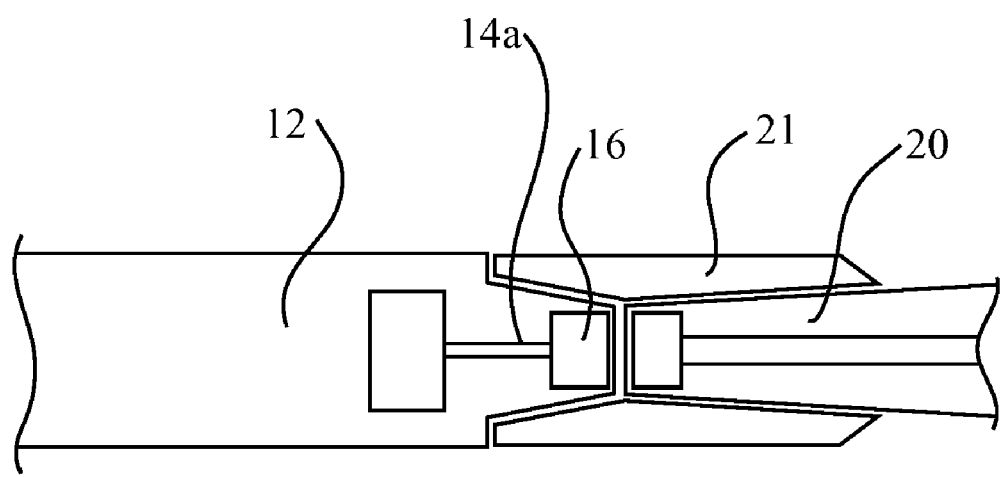
FIG. 3 is a truncated view of a tool assembly mounted to the housing coaxial with the drive shaft of the motor.
Figure 4:
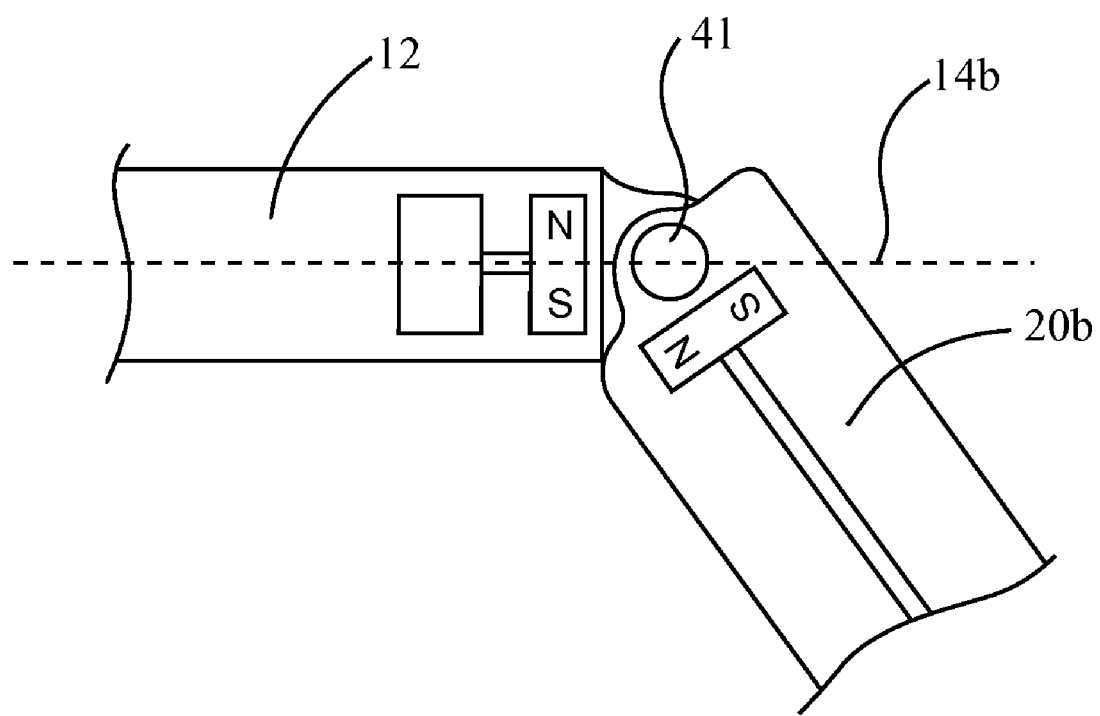
FIG. 4 is a truncated view of a rotatably mounted tool assembly and housing according to the invention.

Turning back to FIG. 1, the mount 18 also defines a female bore 34 for receiving and positioning the tool assembly 20 at a desired angle relative to the drive axis 14b of the motor 14. The angle of the central axis 34a of female bore 34 relative to the drive axis 14b may vary between 0 and 90°, and more preferably 0 and 45° depending on the angle of the tool 24 relative to the drive axis 14b that is desired for access to a treatment site and comfort to the surgeon. If no angle is desired between the central axis 34a and the drive axis 14b, then the tool assembly 20 may be mounted to the housing 12 as shown in FIG. 3 with straight mount 21. The straight mount 21 situates the tool assembly 20 coaxially with the drive axis 14b of the motor shaft 14a and drive magnet 16. It is contemplated that various mounts defining female bores cut at different angles may be substituted into the instrument 10 for different surgical procedures or for different steps of the same surgical procedure. Alternatively, or additionally, as shown in FIG. 4, a tool assembly 20b may be rotatably mounted to the housing 12 via a hinge joint 41 which fixes the tool assembly 20b at different angles relative to the drive axis 14b whereby the tool assembly 20b may be swiveled interaoperatively.

Turning back to FIG. 1, the connection between the tool holder 36 and the tool mount 18 is preferably via an interference fit accommodated by the tapered fit of the tool holder 36 within the bore 34 of the mount 18. The connection may also be in the form of a more secure leur lock, though the direction of tightening is preferably in the same direction of rotation as the tool magnet 22 during operation so as not to loosen the connection between the tool holder 36 and the mount 18. Alternatively, it is contemplated that if the direction of tightening is opposite that of the direction of rotation of the tool magnet 22, then the frictional resistance on the shaft 26 during operation may be reduced at the expense of loosening the leur lock.

The tool assembly 20 preferably includes a tool holder 36, a plastically deformable outer metal tube 38 extending from a proximal end 38a to a distal end 38b of the tool holder, and a continuous bearing sleeve 40 which is preferably fixed within the outer metal tube 38 to the inside surface of the metal tube 38. The tool holder 36 is preferably made from PEEK plastic and surrounds the tool magnet 22. The bearing sleeve 40 is also preferably made from PEEK plastic, and extends from a proximal end 40a inside the tool holder 36, through the metal tube 38, to a distal end 40b beyond the distal end 38b of the metal tube 38. The elongate shaft 26 of the tool assembly 20 extends from a proximal end 26a inside the tool holder 36, through the bearing sleeve 40, to a distal end 26b beyond the distal ends 38b, 40b of the metal tube 38 and the bearing sleeve 40. The shaft 26 is securely supported by but rotatable within the bearing sleeve 40 about a shaft axis coaxial with bore axis 34a, and is preferably made from flexible spring steel wire or tubing with an outer diameter in the range of 0.020 to 0.028 inches. The diameter of the sleeve 40 is preferably small enough to contact the shaft 26 to prevent wobbling or lateral movement of the shaft 26, but not so small as to restrict rotation or longitudinal translation of the shaft 26.

As a portion of the shaft 26 extends beyond the distal edge 40b of the sleeve 40 (e.g. the distal end 26b of the shaft 26 is distal of the sleeve 40), it will be appreciated that the shaft 26 may be slightly bent at the distal end 26b relative to the sleeve 40 during operation if needed. As the shaft 26 is preferably made from flexible spring steel wire, the distal end 26b returns to its original shape once any such deforming force is removed.

The sleeve 40 and support tube 38 may be manually bent along a curve by a surgeon or other user. If the sleeve 40 and support tube 38 are bent by a user, then the portion of the shaft 26 inside of the sleeve 40 and support tube 38 will simply bend with the sleeve 40 and support tube 38. It is nevertheless recommended that a user, rather than significantly bending the tube 38, utilize an appropriate mount 18 designed to orient the tool assembly at the appropriate angle. A user may then bend the tube 38 to make minor directional adjustments as needed.

Figure 5:
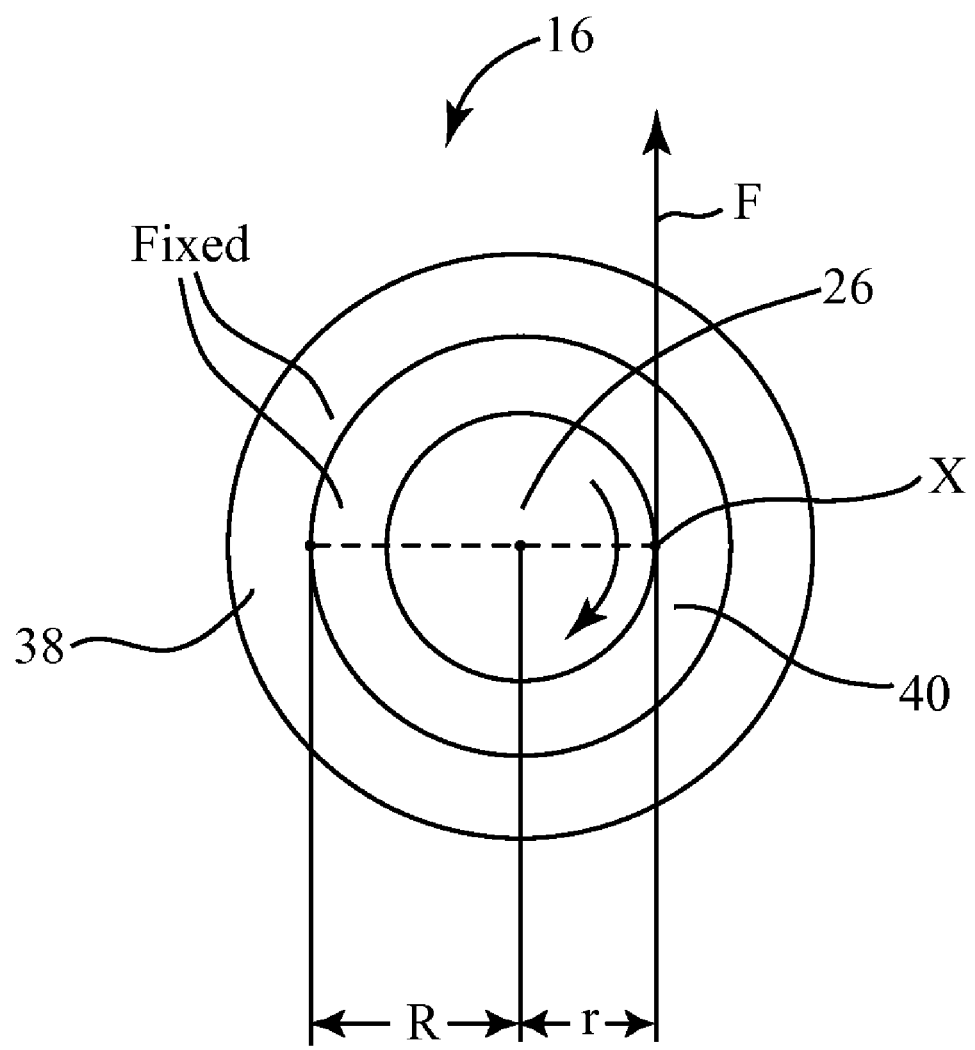
FIG. 5 is a cross sectional view taken along line 3-3 of FIG. 1.

Turning to FIG. 5, the shaft 26, the continuous bearing sleeve 40, and the metal bearing support tube 38 which helps to support the sleeve 40 and shaft 26 are shown. It will be appreciated by those skilled in the art that rotation of the shaft 26 will produce frictional forces between the outer surface of the shaft 26 and the inner surface of the sleeve 40 at, for example, point X as shown in FIG. 4. It will also be appreciated that the torque required to overcome frictional resistance at a single point X on the outer circumference of the shaft 26 is equal to the frictional force (F) applied at point X by the sleeve 40 times the radius (r) of the shaft 26. The frictional force (F) is caused by the normal force between the shaft 26 and the sleeve 40, which is snugly fit around the shaft 26. By attaching the sleeve 40 to the support tube 38 rather than the shaft 26, the radius over which the frictional force acts is reduced from (R) to (r) as shown. Additionally, the frictional resistance will be reduced by the decrease in the total surface area of the contact surfaces. This surface area is approximately equal to $2\Pi rL$, where L is the length of the overlapping surfaces of the sleeve 40 and shaft 26. If the sleeve 26 were instead attached to the shaft 26, then the sleeve 40 and shaft 26 would rotate together, and the area of the contacting surfaces would instead be the area between the outer surface of the sleeve 40 and the inner surface of the tube 38, or $N\Pi RL$. Thus, attaching the sleeve 40 to the support tube 38 rather than to the shaft 26 will decrease the total frictional resistance, and by consequence, the torque required to spin the shaft 26 at a given angular velocity.

Turning back to tool assembly 20 shown in FIG. 1, the tool magnet 22 is preferably situated within the tool holder 36 and fixed to the proximal end 26a of the elongate shaft 26 proximal of the metal tube 38 and bearing sleeve 40. The tool magnet 22 encircles and rotates with the shaft 26 within the tool holder 36, preferably about a tool magnet axis aligned with the shaft axis 14b. Thus, the tool holder 36 defines an open chamber 39 large enough to allow the tool magnet 22 to freely rotate with the proximal end 26a of the shaft 26 inside the chamber 39. The sleeve acts as a thrust bearing for the tool magnet 22, with the sleeve having sufficient structurally strength for such function. The tool magnet 22 is preferably adjacent the proximal edge 40a of the continuous sleeve 40 so that the tool magnet 22 does not wobble when it rotates. The distal side of the tool magnet 22 and the proximal edge 40a of the sleeve 40 are offset by a small gap (roughly 0.1 mm) to help prevent the sleeve 40 from inhibiting rotation of the tool magnet 22. Like the drive magnet 16, the tool magnet 22 is also preferably cylindrically shaped, has a diameter, and is magnetized with opposite polarity (north and south) on opposite sides of the diameter as designated by the letters "N" and "S" in FIG. 1.

In order to achieve the necessary forces for torque transfer in a small space, it is beneficial to utilize rare earth high energy magnets such as neodymium iron boron or samarium cobalt. For example, when each of the drive magnet and tool magnet are a 50 MGO NdFeB magnet of 5 mm in diameter and 5 mm in length, it is possible to separate the drive magnet and tool magnet by a distance of up to 3 mm and still achieve the necessary torque transfer. The high strength of the magnet is important since magnet strength decreases with the cube of the distance from the source. In addition, NdFeB magnets are subject to partial demagnetization at the temperatures reached in a standard autoclave cycle of 121° C. This can be used to advantage, if desired, by sizing the magnets and spacing such that sufficient torque exists to drive the tool before autoclaving but not after. In this manner, a single use rule for disposable cutting instruments can be realized.

The medical tool 24 is fixed to the distal end 26b of the shaft 26, and thus rotates and/or longitudinally translates with the shaft 26. The medical tool 24 may be a cutter, a drill, a file, or any of a number of other similar devices as further discussed below. It will be appreciated that various replaceable mounts and tool assemblies may be used in conjunction with the instrument 10 during one or more medical procedures to change the angle of the tool assembly 20 relative to drive axis 14b as well as the tool 24 which is utilized with the instrument 10.

As shown in FIG. 1, when assembled, the shaft 26 of the tool assembly 20 extends through the tool holder 36 with its proximal end 26a situated near the drive shaft 14a of the motor 14 such that the drive magnet 16 attached to the drive shaft 14a and the tool magnet 22 attached to the proximal end 26a of the shaft 26 are magnetically coupled. It will be appreciated by those skilled in the art that the torque transmission between the drive magnet 16 and the tool magnet 22 may be varied or controlled based on the strength of the magnets used, the size of the magnets used, the diameters of the magnets, and/or the distance between the magnets. As stated above, it is preferred that the drive magnet 16 be mounted to the shaft 14a such that the axis of the drive magnet 16 is collinear with the drive axis 14b, and that the tool magnet 22 be mounted to the elongate shaft 26 such that the axis of the tool magnet 22 is collinear with the shaft axis 26c. This will help to minimize wobbling or vibration in the instrument 10 when the magnets (16, 22) rotate about their respective axes.

It will also be appreciated by those skilled in the art that the drive and tool magnets (16, 22) emit magnetic fields which, absent any shielding, could potentially negatively affect a patient having metal implants or other devices in his or her body. Thus, it is recommended that the male taper portion 30 of the housing 12, the mount 18, and the tool holder 36 be shielded, for example, with a material such as mu-metal in order to provide a path for the magnetic field lines through the mount 18 between the magnets (16, 22) and thus reduce the magnetic flux which escapes the instrument 10.

In operation, the motor 14 of the instrument 10 is activated by push button, switch, foot pedal or other suitable means 61. For example, the foot pedal 61 could be depressed by a user to activate the motor 14 and or change the direction of rotation of the shaft 14a by the motor 14. The motor 14 is powered by an external power source 60 electrically coupled to the motor 14 via the wires 31. The motor 14 may alternatively be powered by batteries 63 (shown in phantom lines) situated within the housing 12. It is also contemplated that the instrument 10 could be activated and operated by wireless means 65 remotely coupled to the external power supply 60 and/or switch/foot pedal 61.

Activation of the motor 14 rotates the drive shaft 14a and drive magnet 16 about the drive axis 14b. Rotation of the drive magnet 16 about the drive axis 14b induces movement of the tool magnet 22 attached to the tool 16 on account of the magnetic coupling between the magnets (16, 22), which in turn causes movement of the shaft 26 and tool 24. In the tool assembly 20 of FIG. 1, the tool magnet 22 cannot longitudinally translate relative to the tool holder 36 or housing 12 but can freely rotate 360 degrees about the shaft axis 26c. Thus, the shaft 26 and tool 24 are also rotatable through 360 degrees about the shaft axis 26c. As shown, the poles (N and S) of the drive magnet 16 are oppositely oriented to the poles (N and S) of the tool magnet 22. This will naturally occur when the drive magnet 16 is rotated and its poles attract the poles of the tool magnet 22.

The structure of the mount 18 and tool assembly 20 in conjunction with the forces applied to the tool magnet 22 via the magnetic coupling between the drive magnet 16 and the tool magnet 22 thus guide the movement of the tool 24 in rotation, oscillation, and/or longitudinal translational on or about the shaft axis 26c.

Figure 6:
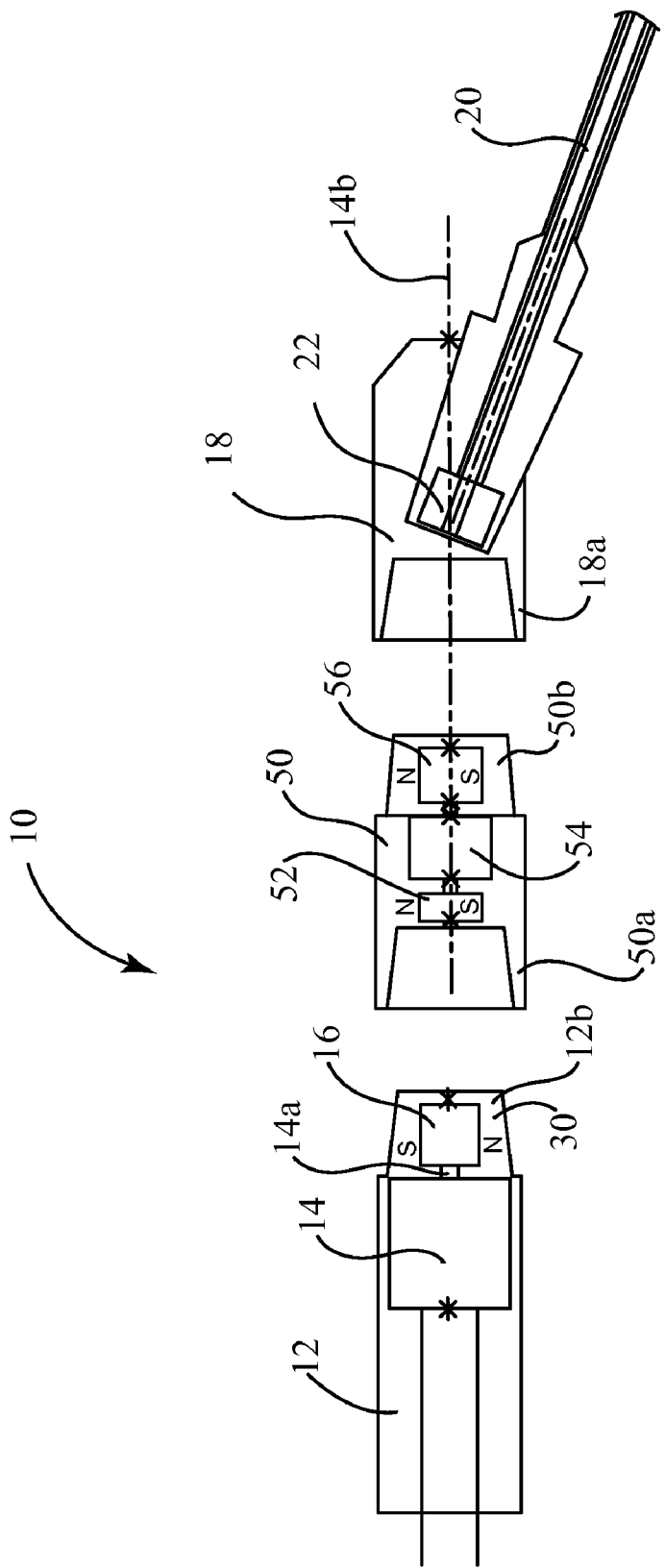
FIG. 6 is a partially exploded schematic view of the invention indicating placement of the speed reducer.

Turning to FIG. 6, a speed reducer 50 is provided for optional placement between the housing 12 and the mount 18. The speed reducer 50 reduces the angular velocity and/or increases torque transferred from the drive magnet 16 to the tool magnet 22. The speed reducer 50 includes an input magnet 52 in magnetic communication with the drive magnet 16, a planetary gear drive 54 mechanically coupled to the input magnet 52, and an output magnet 56 mechanically coupled to the gear drive 54. The proximal end 50a of the speed reducer 50 couples to the male taper portion 30 at the distal end 12b of the housing 12 in the same type of male/female taper lock engagement discussed above with respect to the male taper portion 30 and female portion 32 of FIG. 1. Similarly, the distal end 50b of the speed reducer 50 is shaped in a male taper portion and couples to the proximal end 18a of the mount 18, which detachably couples to the tool assembly 20 as discussed above. The mount 18 and tool assembly 20 position the tool magnet 22 in magnetic communication with the output magnet 56 of the speed reducer 50.

In operation, the motor 14 rotates the drive shaft 14a and drive magnet 16 about the drive axis 14b. The rotating drive magnet 16 induces rotation in the input magnet 52 of the speed reducer 50. Rotation of the input magnet 52 actuates the planetary gear drive 54, which, through a series of mechanical gears (not shown), produces a decreased angular velocity of the output magnet 56. The rotating output magnet 56 induces movement of the tool magnet 22, which causes movement of the tool as discussed above. In this manner, high speed motors which ordinarily would not be suited for a given application may be utilized in medical applications and procedures where lower speeds are preferred by simply selecting the appropriate speed reducer. It will be appreciated by those skilled in the art that the speed reducer 50 could also be used to increase the rotational speed transferred from the motor 14 to the tool 24 (FIG. 1), and that the torque transferred to the tool 24 may similarly be varied or controlled based on the strength, size, diameter, and distance between the magnets (16, 52), (56, 22). It is noted that while the speed reducer magnets (52, 56) are mechanically coupled by the gear drive 54, frictional forces within the gear drive 54 and potential magnetic coupling between the input magnet 52 and the output magnet 54 will provide additional resistance to the motor 14 when the output magnet 56 is rotating with a lower angular velocity than the input magnet 52 (speed reduction), which results in increased torque being transmitted from the motor 14 to the output magnet 56, tool magnet 22, and tool 24.

Figure 7:
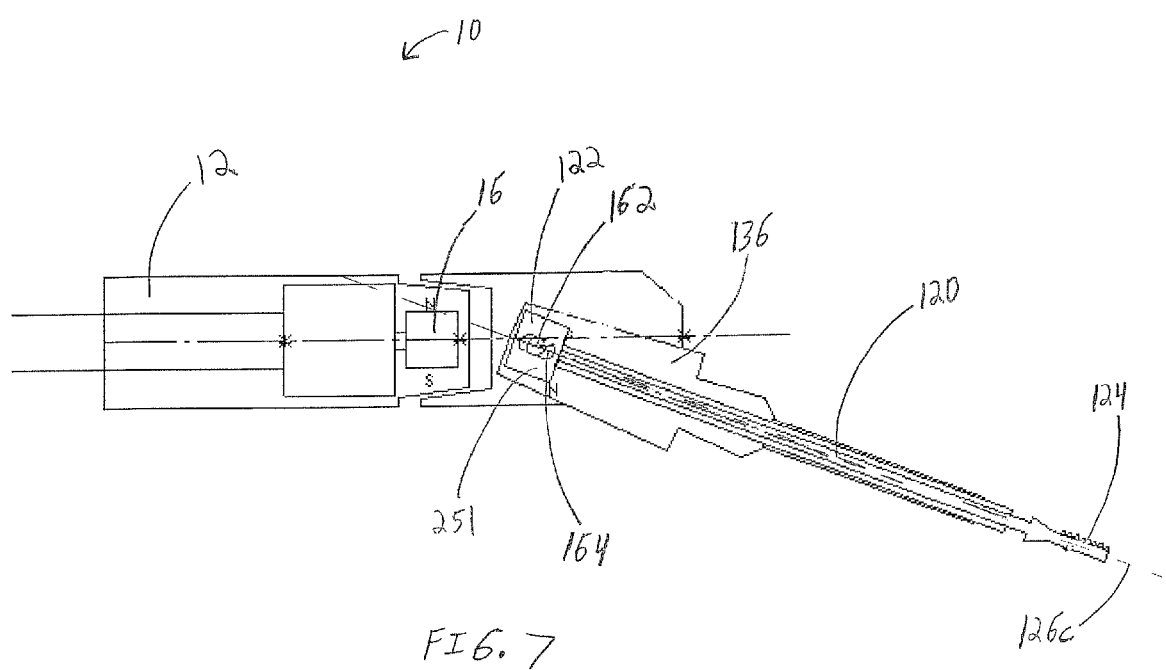
FIG. 7 is a schematic view of the invention incorporating a second tool assembly included in a kit according to the invention.

As discussed above, the invention 10 may utilize one or more mounts and one or more tool assemblies for a given medical procedure or for different medical procedures. The tool assembly 20 allows for rotation of the tool 24 but not longitudinal translation. Turning to FIG. 7, the instrument 10 is shown with a tool assembly 120 which allows for longitudinal translation of the tool 124. The tool assembly 120 includes at least one attachment pin 162 extending from and fixed to at least one side of the tool magnet 122. The tool holder 136 defines at least one slot 164 for slidably receiving the at least one attachment pin 162. The slot 164 extends in a generally parallel direction relative to the shaft axis 126c. This slot 164 thus prevents rotation of the tool magnet 122 and tool 124 about the shaft axis 126c (the pin 162 can only move along the slot 164 in the direction of the shaft axis 126c) while allowing for limited translation of the tool magnet 122 and tool 124 relative to the housing 12 or tool holder 136.

Rotation of the drive magnet 16 applies a force on the tool magnet 122 on account of the magnetic coupling therebetween. As the slot 164 limits movement of the tool 124 to longitudinal translation, the force will translate the tool 124 distally when the poles of the magnets 16, 122 repel each other and proximally when the poles attract each other. Thus, one complete 360° rotation of the drive magnet 16 will cause the tool 124 to move through the translational range allowed by the slot 164, and the RPM of the drive magnet 16 will correspond to the oscillary translation frequency of the tool 124. It will be appreciated by those skilled in the art that the distal most portion of the slot 164 should still place the tool magnet 122 within magnetic reach of the drive magnet 16. Otherwise, the tool magnet 122 could translate out of magnetic reach of the drive magnet 16. It is anticipated that the tool 124 utilized with this type of motion could be a file for filling down bone, though other types of tool known in the art could be utilized.

Figure 8:
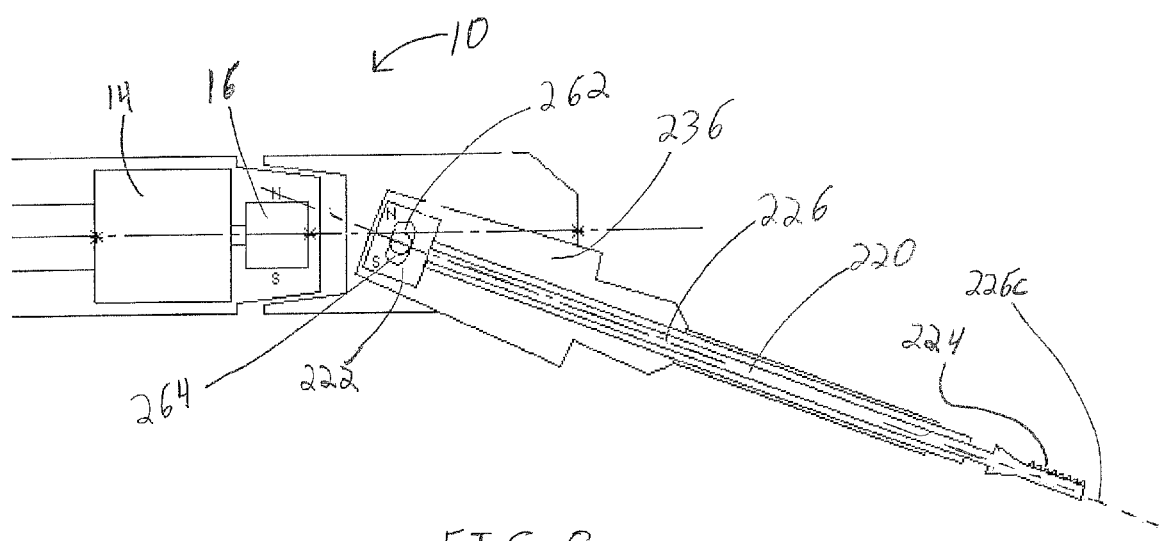
FIG. 8 is a schematic view of the invention incorporating a third tool assembly included in a kit according to the invention.

Turning to FIG. 8, the instrument 10 is shown with another tool assembly 220 which allows for limited rotational movement (oscillation) about the shaft axis 226c but prevents longitudinal translation of the tool 224. The tool assembly 220 includes at least one attachment pin 262 extending from and fixed to at least one side of the tool magnet 222. The tool holder 236 defines a slot 264 which extends in a generally perpendicular direction relative to the shaft axis 226c. This slot 264 thus prevents longitudinal translation of the tool magnet 222 and tool 224 along the shaft axis 226c (the pin 262 can only move along the slot 264 in the direction perpendicular to the shaft axis 226c) while allowing for limited rotation (oscillation) of the tool magnet 222 and the tool 224 about the shaft axis 226c.

Rotation of the drive magnet 16 by the motor 14 applies a force on the tool magnet 222 on account of the magnetic coupling therebetween. As the slot 262 limits movement of the tool 224 to rotational movement, the force will rotate the tool 224 in the direction induced by the drive magnet 16 until the pin 262 reaches the upper or lower limit of the slot 264, at which time the tool 224 will temporarily remain stationary until rotation of the tool magnet 222 (and thus the shaft 226 and tool 224) is induced in the other direction. Thus, one rotation of the drive magnet 16 will cause the tool 224 to move through the rotational range provided by the slot 264, and the RPM of the drive magnet 16 will correspond to the oscillary rotation frequency of the tool 224. It is anticipated that the tool 224 utilized with this type of motion could be a burr or cutter for removing material from the edges of a curved surface (e.g., sinus passages), though other types of tools known in the art could be utilized.

It will therefore be appreciated by those skilled in the art that the invention may be presented as a kit which includes one or more mounts and one or more tool assemblies. Alternatively, separate handpieces and tools may be provided for dedicated procedures.

Figure 9:
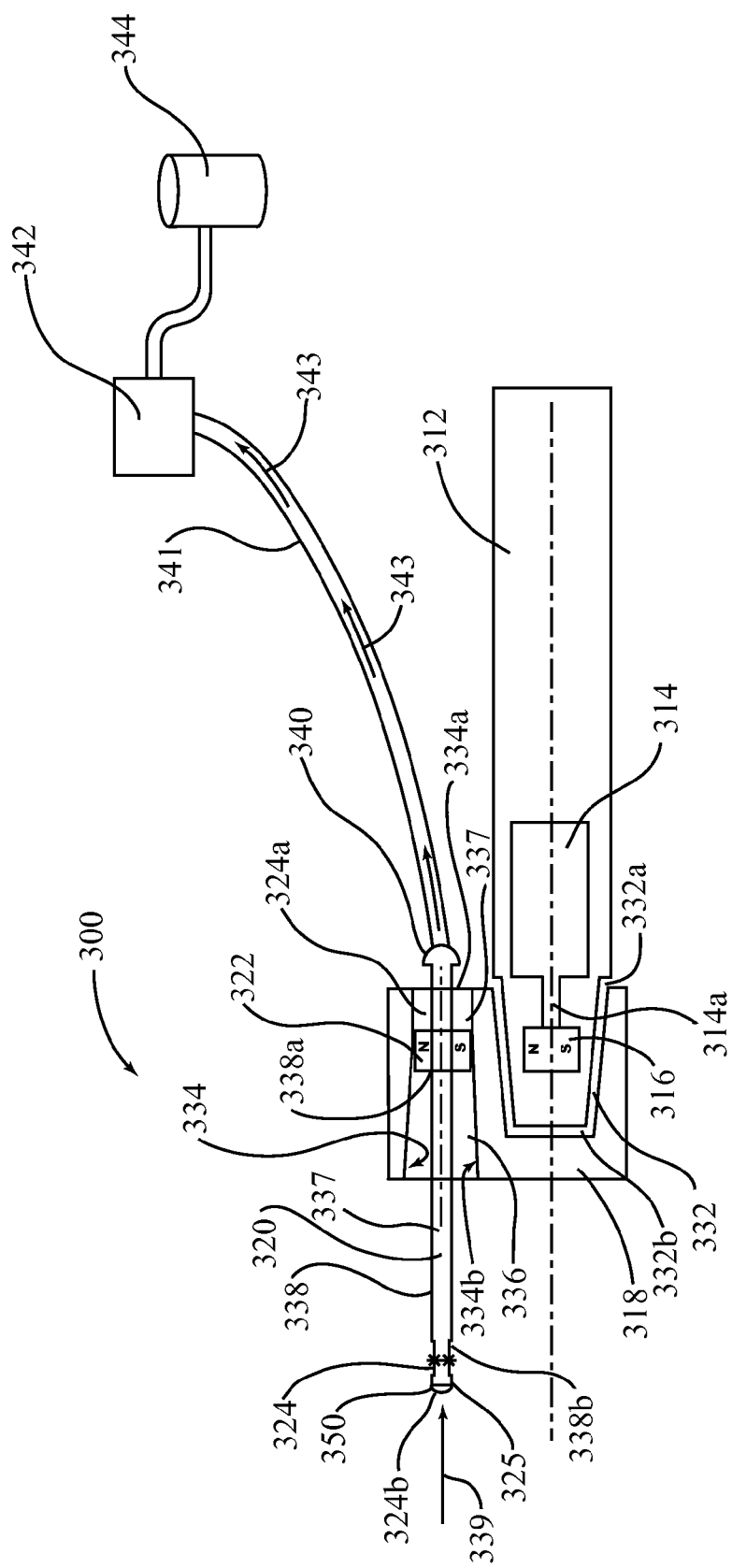
FIG. 9 is a schematic view of another embodiment of the invention in which a fourth tool assembly is in fluid communication with a suction device.

Turning to FIG. 9, an alternative embodiment of the instrument 300 is shown with a tool assembly 320 mounted to the housing 312 via a mount 318 which positions the tool assembly 320 laterally offset from the drive shaft 314a of the motor 314. The tool assembly 320 includes a hollow outer tube 338 extending between proximal and distal ends (338a, 338b), and a hollow inner tube 324 extending from a proximal end 324a through the tool magnet 316, through the hollow outer tube 338 to a distal end 324b. The inner tube 324 is rotatable within the outer tube 338. The tool magnet 322 is rotatably fixed to the hollow inner tube 324 at the proximal end 324a in the same manner that the tool magnet of FIG. 1 is fixed to the solid shaft of the tool holder of FIG. 1. The tool magnet 322 and hollow inner tube 324 are rotatable inside the tool holder 336.

The tool holder 336 includes a suction port 340 disposed at a proximal end of the tool holder 336, and preferably defines a proximal bearing surface 337 between the tool magnet 322 and the port 340. The port 340 is preferably connected to a suction tube 341 in open communication with a suction device 342. The suction device 342 is preferably in fluid communication with a container or other receptacle 344.

The mount 318 defines an upper tapered bore 334 which includes the bearing surface 337, which may be formed as a step in the bore 334. The upper tapered bore 334 extends through the mount 318 between proximal and distal ends (334a, 334b). The mount 318 also includes a lower tapered bore 332 which receives the housing 312. In this configuration, a fluid or other debris present in a patient may be removed during, for example, arthroscopic procedures. Fluid is sucked into the hollow inner tube 324 at arrow 339. The fluid passes through the inner tube 324 and the port 340 into the suction tube 341. The fluid continues through the suction tube 341 in the direction of the arrows 343, passes through the suction device 342 and is ultimately transferred to the receptacle 344.

It will be appreciated that the inner tube 324 may be rotated about its axis in a manner similar to that discussed above with respect to the shaft 26 of FIG. 1 via the magnetic coupling between the drive magnet 316 and the tool magnet 322. It will be appreciated that the mount 318 may be modified to position the tool assembly 320 above or below the motor 314 and drive shaft 314a at different angles so long as the magnetic coupling between the drive magnet 316 and the tool magnet 322 is maintained. It is also noted that the relative positioning of the drive magnet 316 and the tool magnet 322 by the mount 318 will cause the tool magnet 322 to rotate about its axis in a direction opposite that of the drive magnet 316. Magnetic shielding is also optionally provided between the magnets (316, 322) via the mount 318 housing 312, and/or tool holder 336. As discussed above with respect to FIG. 1, various tools may be provided to the distal end 324b of the inner tube 324. For the embodiment of FIG. 9, the "tool" provided at the distal end 324b of the inner tube 324 may simply be the open distal end 324b itself and/or an entry nozzle 350.

It is anticipated that the invention disclosed herein will mitigate a number of factors which limit the longevity and efficacy of medical instruments known in the art. These factors include repeated exposure of internal elements to pressurized steam during sterilization processes, difficulties in cleaning and sterilization due to complex surfaces and numerous interconnected components, alignment and precision requirements of various surgical processes, high levels of frictional heat and resistance generated from moving parts in contact with each other, limited operating parameters inherent in a given tool based on the physical characteristics of the power supply utilized and the types of mechanical and electrical systems used to transmit and convert power, and range of motion limitations on the tool resulting from the difficulties inherent in adjusting the direction of the surgical tool relative to the drive system.

There have been described and illustrated herein several embodiments of a medical instrument. While particular embodiments of the invention have been described, it is not intended that the invention be limited thereto, as it is intended that the invention be as broad in scope as the art will allow and that the specification be read likewise. Thus, while particular shapes and sizes of mounting apparatuses, locking mechanisms, and component parts have been disclosed, it will be appreciated that other shapes and sizes may be used as well. In addition, while particular plastics and metals have been disclosed, it will be understood that other plastics, metals, and other materials known in the art may be used. Also, while a tool containing a tool shaft, bearing sleeve, and metal tube is preferred, it will be recognized that the device will function without the bearing sleeve or the metal support tube. While an electric and/or battery powered motor is disclosed for driving the drive shaft and drive magnet, it will be appreciated that a pneumatic air supply may alternatively be used to rotate the drive magnet. Furthermore, while specifically shaped slots have been disclosed for guiding the direction of the tool, it will be understood that other shaped and sized slots can be similarly used. Moreover, while particular configurations have been disclosed in reference to the angle with which the tool holder is received by the tool adaptor, it will be appreciated that other configurations could be used as well. It will therefore be appreciated by those skilled in the art that yet other modifications could be made to the provided invention without deviating from its spirit and scope as claimed.

What is claimed is:

1. A medical instrument for use on a patient, comprising:
a housing forming an external body of said instrument for manipulation by a user, said housing having a proximal end and a distal end,
a tool mount at said distal end of said housing, said tool mount defining a mounting bore having a proximal end and a distal end;
a motor having a drive shaft rotatable about a drive axis;
a drive magnet fixed to said drive shaft of said motor such that rotation of said drive shaft rotates said drive magnet about said drive axis, wherein said motor, said drive shaft and said drive magnet are hermetically sealed within said housing; and
at least one replaceable tool assembly detachably coupled relative to said drive magnet at said mounting bore of said tool mount, said mounting bore located outside said hermetic seal, said tool assembly formed as a separable unit from said housing and said tool mount, said tool assembly including,
a tool holder releasably received in a proximal direction through said distal end of said mounting bore during coupling of said tool holder to said tool mount, and in a distal direction out of said distal end of said mounting bore during decoupling of said tool holder from said tool mount,
an elongate tool shaft having a tool shaft axis and proximal and distal ends, said tool shaft extending through said tool holder and rotatable about the tool shaft axis,
a tool magnet having a tool magnet axis about which said tool magnet rotates and a diameter, said tool magnet fixed to said proximal end of said tool shaft and movable relative to said tool holder, said tool magnet magnetized with opposite polarity on opposite sides of said diameter, and
a medical tool for interacting with a patient, said medical tool fixed to said distal end of said tool shaft such that said tool magnet axis, said tool shaft and said medical tool are coaxially arranged along said tool shaft axis,
wherein rotation of said drive magnet by said motor induces, via magnetic forces between said drive magnet and said tool magnet, movement of said tool, and when said drive magnet is rotated, said tool holder remains stationary within said mounting bore of said tool mount.

2. A medical instrument according to claim 1, wherein:
the movement of said tool magnet, said tool shaft, and said tool is at least one of 360 degree rotation about said tool shaft axis, oscillary rotation relative to said tool shaft axis, and longitudinal translation relative to said housing.

3. A medical instrument according to claim 1, wherein:
said tool magnet and said drive magnet are shielded to confine the magnetic field produced from said tool and drive magnets.

4. A medical instrument according to claim 1, further comprising:
a resilient sleeve positioned around said housing.

5. A medical instrument according to claim 1, further comprising:
a power source for said motor located remotely from said handle.

6. A medical instrument according to claim 1, further comprising:
a power source for said motor located within said housing.

7. A medical instrument according to claim 1, further comprising:

a foot switch remotely coupled to said motor for at least one of actuating said motor and changing the direction of rotation of said drive shaft of said motor.

8. A medical instrument according to claim 1, further comprising:
said tool mount is a first mount detachably engageable to said distal end of said housing and said proximal end of tool assembly to couple said tool assembly to said housing such that said tool magnetic axis and said drive axis are in a first orientation.

9. A medical instrument according to claim 8, wherein:
said housing includes a male taper portion and said first mount includes a female portion adapted to receive said male taper portion of said housing in a first frictional taper lock.

10. A medical instrument according to claim 9, wherein:
said housing defines a slot proximal of said male taper portion, and said first mount defines a tab extending distally from said female portion, said slot of said housing receiving said tab of said first mount in said first frictional taper lock to prevent rotation of said first mount relative to said housing.

11. A medical instrument according to claim 9, wherein:
said drive shaft of said motor and said drive magnet are operably disposed inside said male taper portion of said housing.

12. A medical instrument according to claim 9, wherein:
said female portion of said first mount defines an expansion slot for allowing said female portion to flex to receive said male taper portion of said housing.

13. A medical instrument according to claim 8, further comprising:
a second tool mount detachably engageable to said distal end of said housing and said proximal end of tool assembly for coupling said tool assembly to said housing such that said tool magnetic axis and said drive axis are in a second orientation different from said first orientation.

14. A medical instrument according to claim 1, wherein:
said tool magnet axis is obliquely oriented relative to said drive axis.

15. A medical instrument according to claim 1, further comprising:
said tool mount is reconfigurable for selectively orienting said tool assembly at various angles relative to said drive axis.

16. A medical instrument according to claim 1, wherein:
said at least one replaceable tool assembly includes a plurality of tool assemblies,
wherein when a first tool assembly of said plurality of tool assemblies is coupled relative to said drive magnet, rotation of said drive magnet causes said tool of said first tool assembly to one of (i) rotate more than the 360° about its tool shaft axis, (ii) rotationally oscillate less than 360° relative to its tool shaft axis, and (iii) longitudinal translate relative to said housing, and
wherein when a second tool assembly of said plurality of tool assemblies is coupled relative to said drive magnet, rotation of said drive magnet causes said tool of said second tool assembly to move in a manner different than said tool of said first tool assembly.

17. A medical instrument according to claim 16, wherein:
said tool holder defines at least one slot, and said tool magnet includes at least one attachment pin extending from and fixed to at least one side of said tool magnet, said at least one pin slidably receivable in said at least one slot for restricting the range of motion of said tool magnet, said tool shaft, and said tool, wherein, rotation of said drive magnet by said motor induces, via the magnetic coupling between said drive magnet and said tool magnet, movement of said tool magnet, said tool shaft, and said tool.

18. A medical instrument according to claim 17, wherein: said at least one slot defined by said tool holder extends in a generally parallel direction relative to said tool shaft axis at said proximal end of said tool shaft, prevents rotation of said tool magnet, said tool shaft, and said tool about said shaft tool axis, and allows limited translation of said tool magnet, said tool shaft, and said tool relative to said housing.

19. A medical instrument according to claim 17, wherein: said at least one slot defined by said tool holder extends in a generally perpendicular direction relative to said tool shaft axis at said proximal end of said tool shaft, prevents translation of said tool magnet, said tool shaft, and said tool relative to said housing, and allows limited rotation of said tool magnet, said tool shaft, and said tool about said tool shaft axis.

20. A medical instrument according to claim 1, wherein: said tool assembly includes a support tube extending through said tool holder, and a bearing sleeve rotationally fixed within said support tube, said bearing sleeve having proximal and distal ends, said proximal end of said sleeve disposed adjacent said tool magnet, said distal end of said sleeve disposed near said distal end of said tool shaft, said tool shaft extending through and movable within said sleeve.

21. A medical instrument according to claim 1, wherein: said tool assembly further includes a proximal port and said distal end of said tool shaft is in fluid communication with and movable relative to said proximal port.

22. A medical instrument according to claim 1, wherein: said tool magnet axis is parallel to and not coaxial with said drive magnet axis.

23. A medical instrument according to claim 1, wherein: rotation of said drive magnet about said drive axis induces rotation of said tool magnet about said tool magnet axis in a direction opposite that of said drive magnet.

24. A medical instrument according to claim 1, wherein: said tool holder is drawn into said tool mount by a magnetic attraction between said drive magnet and said tool magnet.

25. A medical instrument according to claim 24, wherein: said tool magnet is substantially flush-mounted with a proximal end of said tool holder.

26. A medical instrument according to claim 1, wherein: said tool holder has a smooth circumferential surface.

27. A medical instrument according to claim 1, wherein: said mounting bore and said tool holder have corresponding tapered shapes that facilitate insertion of said tool holder into said mounting bore.

28. A medical instrument according to claim 27, wherein: said mounting bore and said tool holder have corresponding frustoconical shapes.

29. A medical instrument according to claim 27, wherein: said tool holder and said tool mount are made from polyetherketone (PEEK).

30. A medical instrument according to claim 1, wherein: said mounting bore has one open end, said open end is located at said distal end of said bore, and said tool assembly can be received into said mounting bore only at said open end.

31. A medical instrument according to claim 1, wherein: said tool assembly is detachably coupled relative to said mounting bore by a combination of friction and magnetic attraction.

32. A medical instrument according to claim 1, wherein: said medical tool is permanently fixed relative to said tool magnet.

33. A replaceable tool assembly for use with a powered medical instrument for use on a body of a patient, the medical instrument having a housing having proximal and distal ends, a motor mounted relative to said housing, the motor having a drive shaft rotatable about a drive axis and a drive magnet fixed to a distal end of the drive shaft, said tool assembly formed as a distinct unit and comprising:
   a) a tool holder defining a bore;
   b) a bearing sleeve rotationally fixed within said bore of said tool holder, said bearing sleeve having proximal and distal ends;
   c) a elongate shaft extending within said bore and through said bearing sleeve, said shaft having proximal and distal ends and a shaft axis extending between said proximal and distal ends, said shaft rotatable relative to bearing sleeve about said shaft axis;
   d) a tool magnet fixed to said proximal end of said shaft within said tool holder, said magnet having a tool magnet axis and a diameter and magnetized with opposite polarity on opposite sides of said diameter, said tool magnet movable relative to said tool holder; and
   e) a tool fixed at said distal end of said shaft for performing a procedure on the body of the patient, wherein movement of said tool magnet along or about said tool magnet axis causes movement of said tool,
   wherein said proximal end of said sleeve is disposed adjacent said tool magnet, said distal end of said sleeve is disposed adjacent said distal end of said shaft, and said shaft extends through and is movable within said sleeve.

34. A replaceable tool assembly according to claim 33, further comprising:
   a plastically deformable support tube fixed at least partially within said bore of said tool holder, said support tube extending distally from said tool holder, said bearing sleeve extending through said support tube, and said shaft extending from said proximal end of said bearing sleeve through and beyond said distal end of said bearing sleeve,
   said bearing sleeve is deformable as said support tube is plastically deformed, and
   wherein said shaft is flexible.

35. A replaceable tool assembly according to claim 33, wherein:
   said tool can one of (i) rotate more than the 360° about its shaft axis, (ii) rotationally oscillate less than 360° relative to its shaft axis, and (iii) longitudinally translate along said shaft axis.

36. A replaceable tool assembly according to claim 33, wherein:
   said tool can one of (i) rotationally oscillate less than 360° relative to its shaft axis, and (ii) longitudinally translate along said shaft axis.

37. A replaceable tool assembly according to claim 33, wherein:
   said tool holder includes at least one slot, and said tool magnet includes a pin extending radially therefrom, said pin slidably received in said at least one slot for restricting the range of motion of said tool magnet, said shaft, and said tool.

38. A replaceable tool assembly according to claim 37, wherein:

said at least one slot defined by said tool holder extends in parallel to said shaft axis at said proximal end of said shaft, prevents rotation of said tool magnet, and permits limited longitudinal displacement of said shaft relative to said tool holder.

39. A replaceable tool assembly according to claim 37, wherein:

said at least one slot defined by said tool holder extends generally transverse to said shaft axis at said proximal end of said shaft and limits the extent of rotational displacement of said tool.

40. A replaceable tool assembly according to claim 33, wherein:

said tool holder includes a tapered proximal end at which it is coupled in an interference fit relative to said housing of said medical instrument.

* * * * *